US012791644B2

(12) United States Patent
Liu et al.

(10) Patent No.: US 12,791,644 B2
(45) Date of Patent: Nov. 10, 2026

(54) METHOD FOR ACQUIRING MR SIGNAL, MR SCANNING SYSTEM, AND STORAGE MEDIUM

(71) Applicant: United Imaging Research Institute of Intelligent Imaging, Beijing (CN)

(72) Inventors: Si-Min Liu, Beijing (CN); Shuo Chen, Beijing (CN); Hua-Lu Han, Beijing (CN)

(73) Assignee: United Imaging Research Institute of Intelligent Imaging, Beijing (CN)

( * ) Notice: Subject to any disclaimer, the term of this patent is extended or adjusted under 35 U.S.C. 154(b) by 137 days.

(21) Appl. No.: 18/398,265

(22) Filed: Dec. 28, 2023

(65) Prior Publication Data

US 2024/0219497 A1 Jul. 4, 2024

(30) Foreign Application Priority Data

Dec. 28, 2022 (CN) ......................... 202211693321.5

(51) Int. Cl.
*A61B 5/055* (2006.01)
*G01R 33/483* (2006.01)
(Continued)

(52) U.S. Cl.
CPC ....... *G01R 33/4835* (2013.01); *G01R 33/565* (2013.01); *G01R 33/5659* (2013.01);
(Continued)

(58) Field of Classification Search
CPC ............ G01R 33/4835; G01R 33/4818; G01R 33/4828; G01R 33/483; G01R 33/561; G01R 33/5611; Y02A 90/30
(Continued)

(56) References Cited

U.S. PATENT DOCUMENTS 10,114,096 B2 * 10/2018 Liu .................... G01R 33/4835
11,899,085 B2 * 2/2024 Ding .................. G01R 33/4818
(Continued)

FOREIGN PATENT DOCUMENTS

CN 105785297 B 11/2019
CN 111239659 A 6/2020
(Continued)

OTHER PUBLICATIONS

Translation of WO-2023169565-A1 (Year: 2023).*
(Continued)

*Primary Examiner* — Eman A Alkafawi
*Assistant Examiner* — Hugo Navarro

(57) ABSTRACT

A method for acquiring MR signal, an MR scanning system, a computer program product, and a non-transitory computer-readable storage medium. The method includes: obtaining the number of slice groups of SMS excitations of a target object, each of the slice groups including multiple slices excited simultaneously by a multi-band RF pulse; adjusting a preset excitation order for a target slice group in response to a determination that the number of the slice groups is an even number to obtain a target excitation order, spatially adjacent slices being not temporally adjacent; performing the multi-band RF pulse on the target object based on the target excitation order; and acquiring data of the SMS excitations of the target object to obtain the MR signals of each slice of the target object, the MR signals of each slice being used for MRI of the target object.

12 Claims, 7 Drawing Sheets

(51) Int. Cl.

| | |
|---|---|
| ***G01R 33/54*** | (2006.01) |
| ***G01R 33/56*** | (2006.01) |
| ***G01R 33/561*** | (2006.01) |
| ***G01R 33/565*** | (2006.01) |
| ***G01V 3/00*** | (2006.01) |

(52) U.S. Cl.

CPC .............. *A61B 5/055* (2013.01); *G01R 33/54* (2013.01); *G01R 33/543* (2013.01); *G01R 33/5602* (2013.01); *G01R 33/5608* (2013.01); *G01R 33/561* (2013.01); *G01R 33/5619* (2013.01)

(58) Field of Classification Search

USPC .......................................................... 324/309

See application file for complete search history.

(56) References Cited

U.S. PATENT DOCUMENTS

| | | | | |
|---|---|---|---|---|
| 2017/0199259 | A1* | 7/2017 | Beck | G01R 33/5611 |
| 2017/0328971 | A1* | 11/2017 | Bilgic | G01R 33/5611 |
| 2019/0277930 | A1 | 9/2019 | Paul et al. | |
| 2021/0096200 | A1* | 4/2021 | Kettinger | G01R 33/3607 |
| 2021/0116527 | A1* | 4/2021 | Zheng | G01R 33/4835 |
| 2021/0325496 | A1* | 10/2021 | Zheng | G01R 33/4835 |
| 2022/0229135 | A1* | 7/2022 | Stemmer | G01R 33/4835 |
| 2022/0369948 | A1* | 11/2022 | Liu | A61B 5/0044 |
| 2022/0400970 | A1* | 12/2022 | Carinci | A61B 5/055 |
| 2022/0413075 | A1* | 12/2022 | Zeller | G01R 33/5611 |
| 2023/0210482 | A1* | 7/2023 | Huang | G01R 33/34076 600/411 |

FOREIGN PATENT DOCUMENTS

| | | | | |
|---|---|---|---|---|
| CN | 112806982 A | | 5/2021 | |
| CN | 109061533 B | | 8/2021 | |
| CN | 113534030 A | | 10/2021 | |
| CN | 113534032 A | | 10/2021 | |
| CN | 113917378 A | | 1/2022 | |
| CN | 114264994 A | | 4/2022 | |
| WO | 2021098690 A1 | | 5/2021 | |
| WO | WO-2023169565 A1 | * | 9/2023 | G06T 7/30 |

OTHER PUBLICATIONS

Su Shi et al., "Preliminary Research on Controlled Aliasing in Parallel Imaging Results in Higher Acceleration", Journal of Integration Technology, vol. 5 No. 3, May 15, 2016, (7 pages).

Lu Shan et al., "Optimization of Selective Radio Frequency Pulses for Simultaneous Multi-Slice MRI", Chinese Journal of Magnetic Resonance, vol. 35, No. 2, Jun. 15, 2018, (9 pages).

Notice of Allowance of CN202211693321.5.

* cited by examiner

METHOD FOR ACQUIRING MR SIGNAL, MR SCANNING SYSTEM, AND STORAGE MEDIUM

CROSS-REFERENCE TO RELATED APPLICATION

The present application claims the priority of Chinese patent application No. 202211693321.5, filed on Dec. 28, 2022, and entitled "METHOD AND DEVICE FOR ACQUIRING MR SIGNAL, MR SCANNING SYSTEM, AND STORAGE MEDIUM", which is incorporated herein by reference in its entirety.

TECHNICAL FIELD

This application relates to the field of magnetic resonance (MR) technology, and in particular to a method for acquiring MR signal, a device for acquiring MR signal, an MR scanning system, and a storage medium.

BACKGROUND

With the development of MR technologies, the simultaneous multi-slice (SMS) excitation technology has emerged. The SMS excitation is an acceleration technology for magnetic resonance imaging (MRI), in which signals of multiple slices may be simultaneously acquired in one excitation by using a slice-selective multi-band radio-frequency (RF) pulse, thereby decreasing the scanning time greatly and improving an imaging speed. In MRI, a slice profile of a slice-selective multi-band RF pulse is not an ideal rectangle, and there is a transition band that will partially excite neighboring slices. When a slice is about to be excited, its transition bands have been lastly partially saturated by neighboring slice profiles, thus resulting in a reduction in the strength of the acquired signal and a reduction in the signal-to-noise ratio.

SUMMARY

Based on this, the present disclosure provides a method for acquiring MR signal, a device for acquiring MR signal, an MR scanning system, a non-transitory computer-readable storage medium, and a computer program product.

In a first aspect, this application provides a method for acquiring magnetic resonance (MR) signal, and the method includes following steps.

The number of slice groups of simultaneous multi-slice (SMS) excitations of a target object are obtained. Each of the slice groups includes multiple slices excited simultaneously by a multi-band radio frequency (RF) pulse.

A preset excitation order for a target slice group is adjusted in response to a determination that the number of the slice groups is an even number to obtain a target excitation order. Spatially adjacent slices are not temporally adjacent after the preset excitation order is adjusted.

The multi-band RF pulse is performed on the target object based on the target excitation order.

Data of the SMS excitations of the target object are acquired to obtain the MR signals of each slice of the target object. The MR signals of each slice are used for magnetic resonance imaging (MRI) of the target object.

In one of the embodiments, the acquiring the number of the slice groups of the SMS excitations of the target object includes following steps.

Scanning parameters of the target object are obtained. The scanning parameters include the number of slices simultaneously excited by the multi-band RF pulse and a total number of slices of the target object.

The number of the slice groups is determined based on the number of the simultaneously excited slices and the total number of the slices of the target object.

In one of the embodiments, before the adjusting the preset excitation order for the target slice group to obtain the target excitation order in response to the determination that the number of the slice groups is the even number, the method further includes setting the preset excitation order.

In one of the embodiments, the setting the preset excitation order includes following steps. Slices of the target object are sequentially numbered with continuous natural numbers respectively based on a spatial position of each of the slices of the target object. The excitation time points of the slice groups in each of which the smallest-numbered slice is an odd-numbered slice are arranged to be before the excitation time points of the other slice groups within each repetition time, or, the excitation time points of the slice groups, in each of which the smallest-numbered slice is an odd-numbered slice, are arranged to be after the excitation time points of the other slice groups within each repetition time. A slice-number difference of each two slices simultaneously excited in the same slice group is an integer multiple of the number of the slice groups.

In one of the embodiments, the target slice group includes a slice group firstly or finally excited within each repetition time.

In one of the embodiments, the adjusting the preset excitation order for the target slice group to obtain the target excitation order in response to the determination that the number of the slice groups is an even number includes following steps.

A plurality of target slice groups are determined based on the number of the slice groups and the number of the multiple slices simultaneously excited in each of the slice groups.

A time sequence of each of the plurality of target slice groups is adjusted based on the preset excitation order to obtain the target excitation order.

In one of the embodiments, the adjusting the time sequence of each of the plurality of target slice groups based on the preset excitation order to obtain the target excitation order includes adjusting the time sequence of each of the plurality of target slice groups by a time-sequence adjustment amount of each of the plurality of target slice groups based on the preset excitation order to obtain the target excitation order. The time-sequence adjustment amounts of the plurality of target slice groups for adjusting the preset excitation order are different from each other, the time sequence adjustment amount of each of the plurality of target slice groups is less than a preset value, and the preset value is determined based on the number of the slice groups.

In one of the embodiments, the preset value is determined based on a total number of the slices of the target object, the number of the multiple simultaneously excited slices, the number of the slice groups, an acquisition time period corresponding to an excitation of each of the slice groups, and a repetition time.

In one of the embodiments, the determining the plurality of target slice groups based on the number of the slice groups and the number of the multiple slices simultaneously excited in each of the slice groups includes: determining slice groups including slices numbered with $N_S/M_B \times n-i$ to be the plurality of target slice groups, where: $N_S$ denotes a total number of the slices of the target object, $M_B$ denotes the number of the multiple simultaneously excited slices, $Ns/M_B$ denotes the number of the slice groups, i is any integer from 0 to $Ns/M_B/2$-3, and n is any integer from 1 to $M_B$.

In one of the embodiments, the adjusting the time sequence of each of the plurality of target slice groups based on the preset excitation order to obtain the target excitation order includes: moving the time sequences of the plurality of target slice groups including the slices numbered with $N_S/M_B \times n-i$ forwards by time values of $T_{unit} \times (Ns/M_B/2-2-i)$ respectively to obtain the target excitation order, where $T_{unit}=TR/(Ns/M_B)$ is an acquisition time period corresponding to an excitation of each of the slice groups and defined as the unit acquisition time, and TR denotes a repetition time.

In one of the embodiments, after the obtaining the number of slice groups of the simultaneous multi-slice (SMS) excitations of the target object, and before the acquiring the data of the SMS excitations of the target object to obtain the magnetic resonance (MR) signals of each slice of the target object, the method further includes: performing the multi-band RF pulse on the target object based on the preset excitation order in response to a determination that the number of the slice groups is an odd number.

In the second aspect, the present application provides a device for acquiring MR signal. The device includes: an obtainment module for the number of slice groups, an excitation order adjusting module, a first excitation module, and an object imaging module.

The obtainment module for the number of slice groups is configured to obtain the number of slice groups of SMS excitations of a target object.

The excitation order adjusting module is configured to adjust a preset excitation order for a target slice group in response to a determination that the number of the slice groups is an even number, to obtain a target excitation order. In the target excitation order, slices spatially adjacent are not temporally adjacent.

The first excitation module is configured to perform the multi-band RF pulse on the target object based on the target excitation order.

The object imaging module is configured to acquire data of the SMS excitations of the target object to obtain MR signals of each slice of the target object. The MR signals of each slice are used for MRI of the target object.

In the third aspect, the present application provides an MR scanning system. The system includes an MR scanning device and a processing unit. The MR scanning device is configured to emit a multi-band radio frequency (RF) pulse to perform simultaneous multi-slice (SMS) excitations on a target object, and configured to acquire data of the SMS excitations of the target object to obtain MR signals of each slice of the target object. The processing unit is connected to the MR scanning device and has a computer program stored therein. The processing unit, when executing the computer program, performs the steps of the above method.

In the fourth aspect, the present application provides a non-transitory computer-readable storage medium, having executable instructions stored therein. The executable instructions, when being executed by a processor, causes the processor to perform the steps of the above method.

In a fifth aspect, the present application provides a computer program product. The computer program product includes a computer program. The computer program, when being executed by a processor, causes the processor to perform steps of the above method.

In the method and the device for acquiring MR signal, the MR scanning system, the computer readable storage medium, and the computer program product, the number of the slice groups of the SMS excitations of the target object is obtained. Each slice group includes multiple slices that are excited simultaneously by the multi-band RF pulse. When it is determined that the number of the slice groups of the SMS excitations is an even number, the preset excitation order is adjusted for the target slice group, so that the obtained target excitation order satisfies that slices temporally adjacent are not spatially adjacent, thereby reducing the inter-slice cross-talk. The multi-band RF pulse is performed on the target object based on the target excitation order. The data of the SMS excitations are acquired, and the MR signals of each slice of the target object are obtained and used for the MRI of the target object, thereby improving the quality of the acquired signals, increasing the signal-to-noise ratio, and improving the final effect of MRI.

DETAILED DESCRIPTION OF THE EMBODIMENTS

In order to make the purposes, technical solutions and advantages of the present application clearer and to be better understood, the present application will be further described in detail hereinafter with reference to the drawings and embodiments. It should be understood that the specific embodiments described herein are only used to explain the present application but not intended to limit the present application.

The simultaneous multi-slice (SMS) excitation is an acceleration technology for MRI, in which signals of multiple slices may be simultaneously acquired in one excitation, thereby decreasing the scanning time greatly and improving the imaging speed.

In MRI, a slice profile of a multi-band RF pulse for a slice selection is not an ideal rectangle, but there is a transition area between the slice profile and an adjacent slice. When a slice is excited, a signal saturation will occur in the transition area of the adjacent slice, thus resulting in a reduction in the strength of the acquired signal and a reduction in the signal-to-noise ratio. This phenomenon is called inter-slice cross-talk. In order to reduce the inter-slice cross-talk, a sufficient longitudinal relaxation time needs to be reserved for the saturated transition region. In multi-slice imaging, an acquiring manner of alternately exciting odd-and-even-numbered slices is usually used to reduce the inter-slice cross-talk. However, in some cases, this method cannot be applied to imaging by means of a plurality of SMS excitations. Existing methods of a plurality of SMS excitations or traditional methods have the problem of poor imaging effects.

This application provides a method for acquiring MR signal, a device for acquiring MR signal, an MR scanning system, a non-transitory computer-readable storage medium, and a computer program product for imaging by means of a plurality of SMS excitations. This application optimizes the excitation orders of slices and reduce the inter-slice cross-talk in the imaging by means of the plurality of SMS excitations to the greatest extent.

Figure 1:
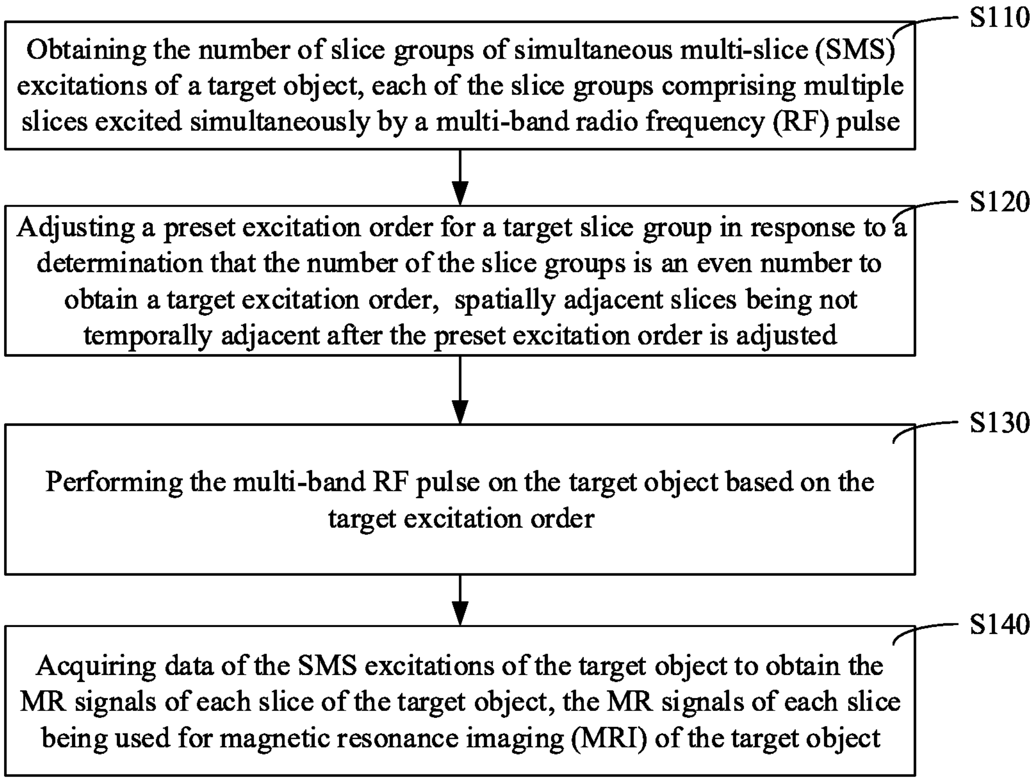
FIG. 1 is a schematic flow chart of a method for acquiring MR signal according to an embodiment of the present application.

In an embodiment, as shown in FIG. 1, a method for acquiring MR signal is provided. The method includes steps S110 to S140.

In step S110, the number of slice groups of SMS excitations of a target object is obtained, where, each slice group includes multiple slices that are excited simultaneously by a multi-band radio frequency (RF) pulse.

Specifically, the multiple slices of the target object may be excited simultaneously by the multi-band RF pulse using the SMS scanning technology. For example, within each a relatively long repetition time (TR), a plurality of excitations may be performed, and a group of slices, namely a slice group may be excited at a time, so that all slices of the multiple slice groups of the target object may be excited, and the respective MR signals may be acquired, thereby increasing the MR scanning speed.

It should be noted that, in MRI, a method for optimizing an excitation order of multi-slice imaging of a single frequency band may be used. For example, in the acquiring manner of alternately exciting odd-and-even-numbered slices: in a relatively long repetition time (TR), firstly, the slice groups, in each of which the smallest-numbered slice is an odd-numbered slice, are excited based on a slice-group sequence, and the corresponding MR signals are acquired at the same time; then other slice groups are excited based on another slice-group sequence, and the corresponding MR signals are acquired at the same time. Alternatively, the slice groups, in each of which the smallest-numbered slice is an even-numbered slice are excited firstly, and then the other slice groups are excited, until all the slices are excited, and the corresponding MR signals are acquired while the slices are being excited. The numbers may be obtained by sequentially sorting the slices of the target object based on the spatial positions of the slices to be imaged. A slice has the same excitation order in all repetition times, for example, a slice 1 has the first excitation order in all repetition times TR. Through the above method, the speed of MR scanning may be increased, and the transition region between spatially adjacent slices has a longitudinal relaxation time of approximate TR/2.

Further, the number of the slice groups may be the number of times multiple slices of the target object are excited simultaneously by the multi-band RF pulse within one repetition time. By obtaining the number of the slice groups, the excitation order of the SMS excitations for the target object may be adjusted appropriately, thereby reducing the inter-slice cross-talk.

In step S120, a preset excitation order is adjusted for a target slice group in response to a determination that the number of the slice groups is an even number, to obtain a target excitation order. In the target excitation order, spatially adjacent slices are not temporally adjacent after the preset excitation order is adjusted.

Figure 2:
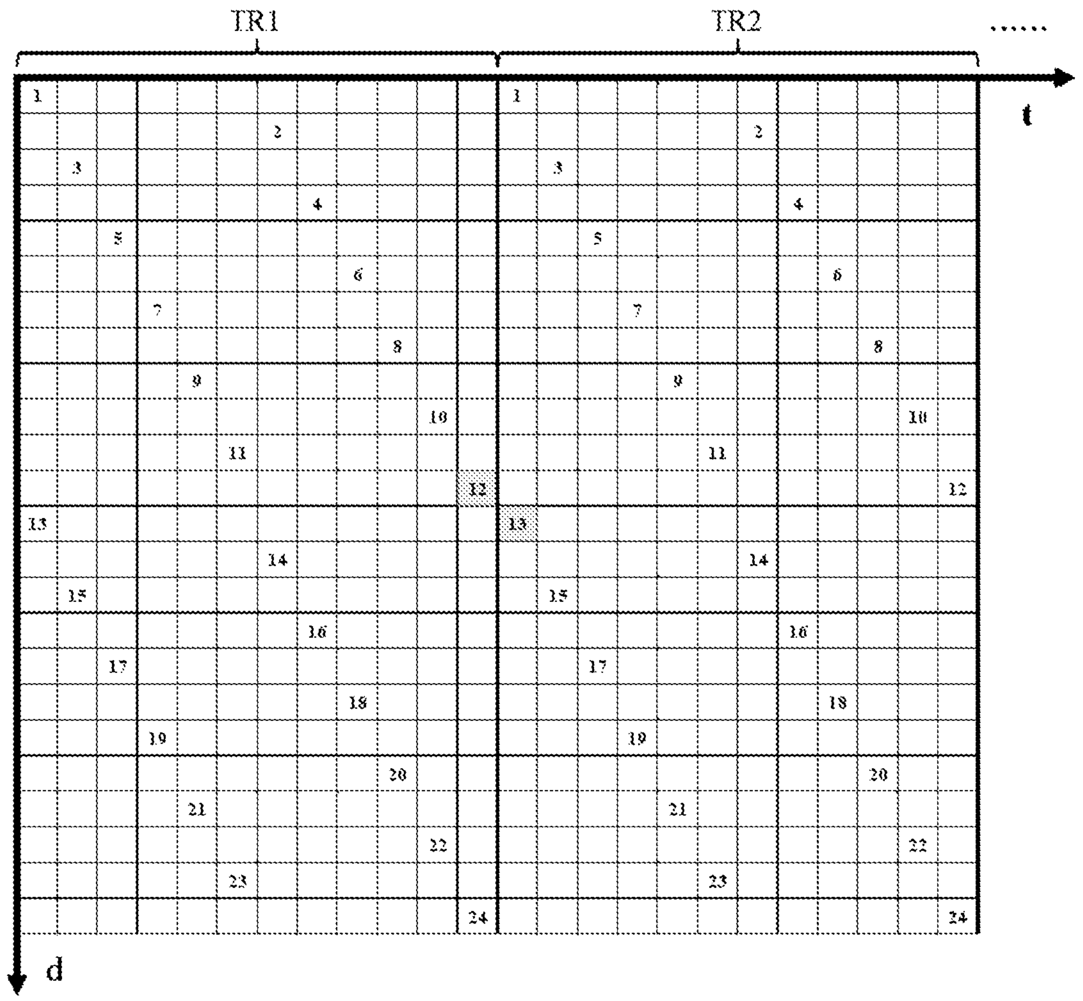
FIG. 2 is a diagram showing a preset excitation order according to an embodiment of the present application.

In some embodiments, the preset excitation order of the multi-band RF pulse uses the acquiring manner of alternately exciting odd-and-even-numbered slices. As shown in FIG. 2, an abscissa t represents a time dimension, and an ordinate d represents a spatial dimension. The total number of slices to be imaged of the target object is 24. Based on the spatial positions of all slices of the target object, the slices of the target object are numbered in sequence with continuous natural numbers, respectively. The multi-band RF pulse may excite two slices of the target object simultaneously, and within one repetition time TR (for example, a first repetition time TR1), the number of the slice groups, namely the number of times slices are excited, are 12. For two adjacent repetition times TR, for example, the first repetition time TR1 and the second repetition time TR2, the slice group finally excited in the first repetition time TR1 includes a slice 12 and a slice 24, and the slice group firstly excited in the second repetition time TR2 includes a slice 1 and a slice 13. As can be seen from FIG. 2, in this preset excitation order, the slice 12 and the slice 13 are not only temporally adjacent in the excitation order, but also spatially adjacent in the spatial positions, therefore there are more distinct signal saturation effects on the slice 12 and the slice 13 between the two repetition times TR, thus causing distinct inter-slice cross-talk, which exhibits that the intensity of the acquired signal of the slice 13 is distinctly lower than those of other slices. Therefore, it is necessary to adjust the excitation order of the plurality of SMS excitations for the target object, so that slices, which are spatially adjacent in the space positions, are prevented from being temporally adjacent in the excitation order, thereby reducing the inter-slice cross-talk.

The acquiring manner of alternately exciting odd-and-even-numbered slices is not applicable to the imaging by means of the plurality of SMS excitations in some cases. For example, in the MRI by means of the plurality of SMS excitations, when the number of the slice groups is an even number, for two adjacent repetition times TR, in the slice group finally excited in the previous repetition time TR, and in the slice group firstly excited in the next repetition time, some slices are spatially adjacent, therefore there are more distinct signal saturation effects on the slices which are temporally adjacent and spatially adjacent between the two repetition times TR, thus causing distinct inter-slice cross-talk, reducing the strength of MR acquisition signals for these slices, and affecting the quality of the images acquired by MRI. The preset excitation order may be an excitation order of the acquiring manner of alternately exciting odd-and-even-numbered slices of the target object. When it is determined that the number of the slice groups is an even number, the preset excitation order may be adjusted for the target slice group to obtain the target excitation order. In some embodiments, the target slice group includes a slice group firstly or finally excited within each repetition time. By adjusting the time sequence of the target slice group in the preset excitation order, the target excitation order is obtained. By adjusting the time sequence of the target slice group, the slices in the slice group finally excited in a previous repetition time and the slices in the slice group firstly excited in the next repetition time of the multi-band RF pulse in the preset excitation order may not be temporally adjacent in the target excitation order, so that the slices spatially adjacent in the spatial positions are not temporally adjacent in the target excitation order, thereby reducing the inter-slice cross-talk.

In some embodiments, as shown in FIG. 2, the preset excitation order may be a sequence in which following slice groups are excited sequentially within one repetition time: a first slice group including a slice 1 and a slice 13, a second slice group including a slice 3 and a slice 15, a third slice group including a slice 5 and a slice 17, a fourth slice group including a slice 7 and a slice 19, a fifth slice group including a slice 9 and a slice 21, a sixth slice group including a slice 11 and a slice 23, a seventh slice group including a slice 2 and a slice 14, an eighth slice group including a slice 4 and a slice 16, a ninth slice group including a slice 6 and a slice 18, a tenth slice group including a slice 8 and a slice 20, an eleventh slice group including a slice 10 and a slice 22, and a twelfth slice group including a slice 12 and a slice 24. In some embodiments, in order to make the slice 12 excited in the first repetition time TR1 and the slice 13 excited in the second repetition time TR2 not temporally adjacent, the time sequence of the twelfth slice group including the slice 12 and the slice 24, or the time sequence of the first slice group including the slice 1 and the slice 13 in the preset excitation order may be adjusted to obtain the target excitation order, in which the slice 12 and the slice 13 are no longer temporally adjacent, thus reducing the inter-slice cross-talk occurring between the slice 12 and the slice 13 in the traditional method.

In step S130, the multi-band RF pulse is performed on the target object based on the target excitation order.

Specifically, the multi-band RF pulse may be performed on the target object based on the target excitation order obtained by adjusting the preset excitation order, and then the SMS excitations are performed on the target object according to the target excitation order, so that the MR signals of each slice of the target object are obtained. By performing the SMS excitations on the target object based on the target excitation order, the problem of the inter-slice cross-talk caused by performing the SMS excitations on the target object based on the preset excitation order can be avoided.

In step S140, data of the SMS excitations of the target object are acquired, and MR signals of each slice of the target object are obtained. Where the MR signals of each slice are used for MRI of the target object.

Specifically, the data of the SMS excitations of the target object may be acquired. The data of the SMS excitations may include the MR signals of each slice of the target object. The MR signals of each slice may be used for the MRI of the target object. By acquiring the data of the SMS excitations of the target object, the MR signals of each slice of the target object are obtained and used for the MRI of the target object, thereby improving the imaging effect of the target object.

In the embodiment of this application, the number of the slice groups of the SMS excitations of the target object is acquired, where, each slice group includes multiple slices that are excited simultaneously by the multi-band RF pulse. When it is determined that the number of the slice groups of the SMS excitations is an even number, the preset excitation order is adjusted for the target slice group, so that the obtained target excitation order satisfies that slices temporally adjacent are not spatially adjacent, thereby reducing the inter-slice cross-talk. The multi-band RF pulse is performed on the target object based on the target excitation order. The data of the SMS excitations are acquired, and the MR signals of each slice of the target object are obtained and used for the MRI of the target object, thereby improving the quality of the acquired signals, increasing the signal-to-noise ratio, and improving the final effect of MRI.

In an embodiment of the present application, after obtaining the MR signals of each slice of the target object, the MR signals of each slice of the target object are processed to obtain images of MR of the target object. Further, the images of MR of the target object are inputted into a monitor, and the monitor displays the images of the target object.

Figure 3:
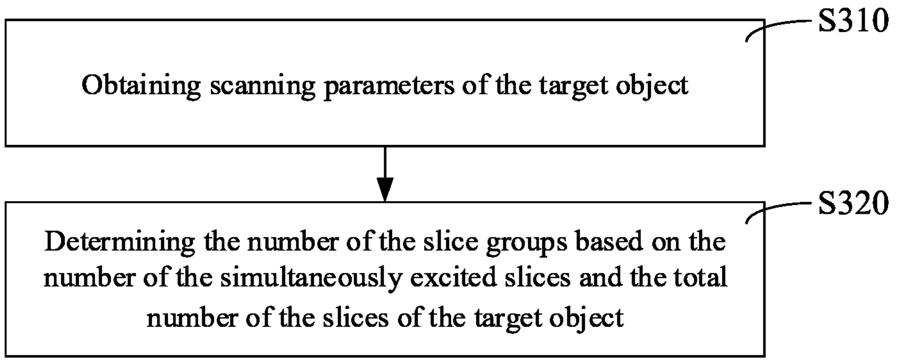
FIG. 3 is a schematic flow chart of a step of the method for acquiring MR signal according to an embodiment of the present application.

In an embodiment, as shown in FIG. 3, step S110 of obtaining the number of the slice groups of the SMS excitations of the target object includes step S310 and step S320.

In step S310, scanning parameters of the target object are obtained. The scanning parameters include the number of slices simultaneously excited by the multi-band RF pulse at a time and a total number of slices of the target object.

In step S320, the number of the slice groups is determined based on the number of the simultaneously excited slices and the total number of the slices of the target object.

Specifically, the number of the slices simultaneously excited by the multi-band RF pulse at a time and the total number of the slices of the target object may be set according to the imaging requirements for scanning the target object. For the target object, $M_B$ denotes the number of the slices that may be excited simultaneously by the multi-band RF pulse at a time, the number of the slice groups may be obtained based on the total number $N_S$ of the slices of the target object and the number $M_B$ of the simultaneously excited slices of the target object. For example, the number of the slice groups may be obtained by dividing the total number $N_S$ of the slices of the target object by the number $M_B$ of the simultaneously excited slices. The scanning parameters may be set flexibly, thereby maintaining the signal-to-noise ratio and the contrast of the images generated by the acquired MR signals without prolonging the scanning.

In some embodiments, when a result obtained by dividing the total number $N_S$ of the slices of the target object by the number $M_B$ of the simultaneously excited slices is not an integer, the result is rounded to obtain the number of the slice groups.

In an embodiment, before step S120 of adjusting the preset excitation order for the target slice group in response to the determination that the number of the slice groups is an even number to obtain the target excitation order, the method further includes setting the preset excitation order. The setting the preset excitation order includes steps of: sequentially numbering the slices of the target object with continuous natural numbers respectively based on the spatial position of each of the slices of the target object, and within one repetition time, arranging excitation time points of slice groups, in each of which the smallest-numbered slice is an odd-numbered slice, to be all before excitation time points of other slice groups, or arranging the excitation time points of the slice groups, in each of which the smallest-numbered slice is an odd-numbered slice, to be all after the excitation time points of the other slices. In the preset excitation order, a slice-number difference of each two slices simultaneously excited in the same slice group is an integer multiple of the number of the slice groups.

Specifically, based on the spatial position of each of the slices of the target object, the slices of the target object may be numbered sequentially with continuous natural numbers respectively to determine each slice number. For the preset excitation order, within one repetition time, after exciting all of the odd-numbered slices, the multi-band RE pulse excites the even-numbered slices, that is to say, the excitation time points of slice groups, in each of which the smallest-numbered slice is an odd-numbered slice, are all before the excitation time points of slice groups, in each of which the smallest-numbered slice is an even-numbered slice. Alternatively, after exciting all of the slice groups, in each of which the smallest-numbered slice is an even-numbered slice, the multi-band RF pulse excites the slice groups, in each of which the smallest-numbered slice is an odd-numbered slice, that is to say, the excitation time points of the slice groups, in each of which the smallest-numbered slice is an odd-numbered slice, are all after the excitation time points of the slice groups, in each of which the smallest-numbered slice is an even-numbered slice. In the preset excitation order, the excitation time points of the slices that are excited simultaneously in the same slice group are the same. The slice-number difference of each two slices simultaneously excited in the same slice group is an integer multiple of the number of the slice groups, so that there is a certain spatial distance between the slices excited simultaneously. Through the preset excitation order above, a preliminary sort of the excitation order of the slices of the target object is realized, which facilitates a targeted adjustment of the excitation order of the slices of the target object, thus avoiding the problem of the inter-slice cross-talk caused by the SMS excitations performed based on the preset excitation order.

In some embodiments, as shown in FIG. 2, the slices included in each slice group are excited simultaneously. Each slice group includes two slices. The slice-number difference of the two slices in each slice group is 12, which is an integer multiple of the number (namely 12) of the slice groups to be excited. The preset excitation order may be the order in which following slice groups are excited sequentially within one repetition time: the first slice group including the slice 1 and the slice 13, the second slice including the slice 3 and the slice 15, the third slice group including the slice 5 and the slice 17, the fourth slice group including the slice 7 and the slice 19, the fifth slice group including the slice 9 and the slice 21, the sixth slice group including the slice 11 and the slice 23, the seventh slice group including the slice 2 and the slice 14, the eighth slice group including the slice 4 and the slice 16, the ninth slice group including the slice 6 and the slice 18, the tenth slice group including the slice 8 and the slice 20, the eleventh slice group including the slice 10 and the slice 22, and the twelfth slice group including the slice 12 and the slice 24, such that within one repetition time, slices spatially adjacent in the spatial positions are not temporally adjacent in the time dimensions.

Figure 4:
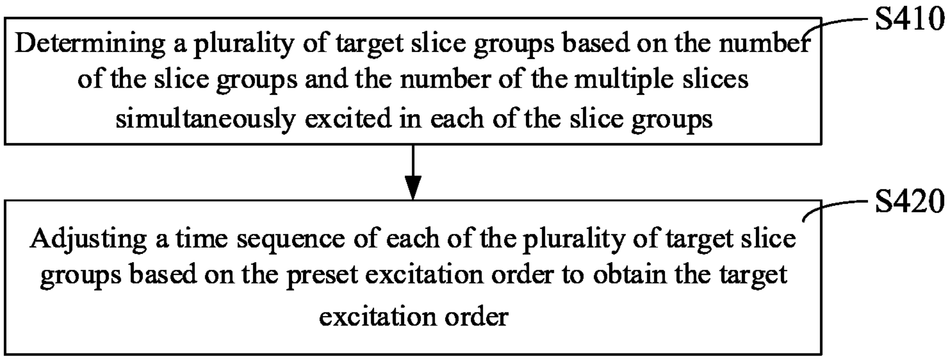
FIG. 4 is a schematic flow chart of a step of the method for acquiring MR signal according to another embodiment of the present application.

In an embodiment, as shown in FIG. 4, step S120 of adjusting the preset excitation order for the target slice group in response to the determination that the number of slice groups is the even number to obtain the target excitation order includes step S410 and step S420.

In step S410, a plurality of target slice groups are determined based on the number of the slice groups and the number of slices simultaneously excited in each of the slice groups.

In step S420, the time sequence of each of the target slice groups is adjusted based on the preset excitation order to obtain the target excitation order.

Specifically, the plurality of target slice groups may be determined based on the number $Ns/M_B$ of the slice groups of the SMS excitations, where each target slice group includes $M_B$ slices excited simultaneously and having the same time sequence. For example, each target slice group may include slices numbered with following numbers: $N_S/M_B\times1-i$, . . . , $N_S/M_B\times(M_B-1)-i$ $N_S/M_B\times M_B-i$, where i may be any integer from 0 to $N_S/M_B$ 2−3, namely, the number of the target slice groups is $N_S/M_B$ 2−2. That is, the slice groups include the target slices numbered with $N_S/M_B\times n-i$, where, n is any integer from 1 to $M_B$. The time sequence of each target slice group may be adjusted based on the preset excitation order. For example, for the target slices numbered with $N_S/M_B\times1-i$, . . . , $N_S/M_B\times(M_B-1)-i$, $N_S/M_B\times M_B-i$, the time sequences thereof are moved forward by time values of $T_{unit}\times(Ns/M_B/2-2-i)$ respectively to obtain the target excitation order. In the target excitation order, for any two spatially adjacent slices, the excitation interval in the time dimension is at least $T_{unit}\times\text{floor}(Ns/M_B/2)-i$, where $T_{unit}=TR/(Ns/M_B)$ is an acquisition time period corresponding to the excitation of each slice group, and is referred to as a unit acquisition time, where TR represents a repetition time, and floor( ) represents a rounding down function. By adjusting each determined target slice group, the transition region between each excited slice and an adjacent slice thereof has sufficient longitudinal relaxation time, thereby reducing the inter-slice cross-talk to the greatest extent.

Figure 5:
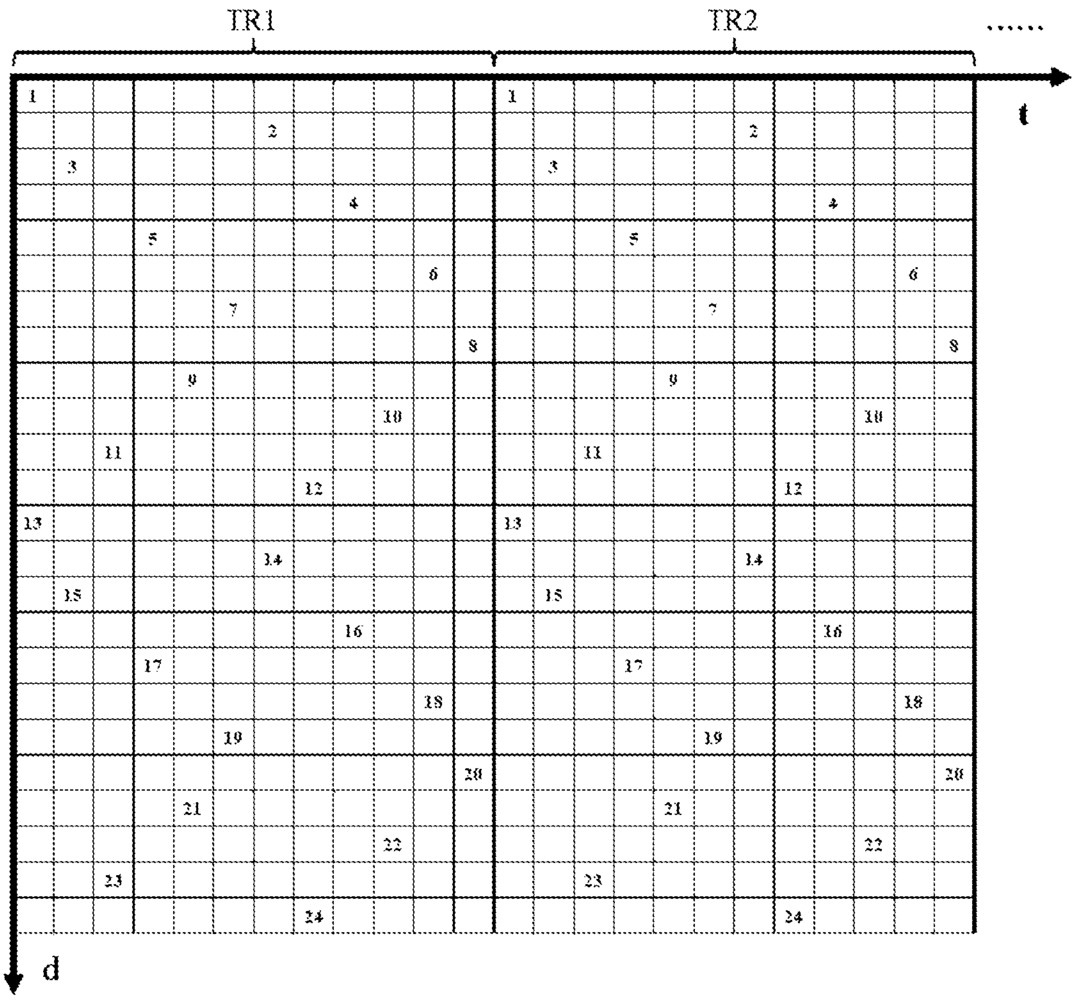
FIG. 5 is a diagram showing a target excitation order according to an embodiment of the present application.

In some embodiments, as shown in FIG. 5, taking $N_S=24$, and $M_B=2$ as an example, FIG. 5 is a diagram showing the adjusted target excitation order. Based on the number (namely 12) of the slice groups and the number (namely 2) of slices simultaneously excited in each slice group, the target slice groups are determined. The target slice groups include the twelfth slice group including the slice 12 and the slice 24, the sixth slice group including the slice 11 and the slice 23, the eleventh slice group including the slice 10 and the slice 22, and the twelfth slice group including the slice 9 and the slice 21. The time dimension of the twelfth slice group including the slice 12 and the slice 24 in the preset excitation order may be moved forward by 4 units of acquisition time, and the time dimension of the sixth slice group including the slice 11 and the slice 23 in the preset excitation order may be moved forward by 3 units of acquisition time, and the time dimension of the eleventh slice group including the slice 10 and the slice 22 in the preset excitation order may be moved forward by 2 units of acquisition time, and the time dimension of the fifth slice group including the slice 9 and the slice 21 in the preset excitation order may be moved forward by 1 unit of collection time, such that the target excitation order is obtained. After being sorted and optimized, the spatially adjacent slices are excited at a time interval of at least $5T_{unit}$ in the time dimension, namely 5 units of acquisition time, within each repetition time or between adjacent repetition times, thereby reducing the inter-slice cross-talk to the greatest extent.

In one of the embodiments, step S420 of adjusting the time sequence of each of the target slice groups based on the preset excitation order to obtain the target excitation order, includes the following steps.

The time sequence of each target slice group is adjusted by a corresponding time-sequence adjustment amount based on the preset excitation order, to obtain the target excitation order. For adjusting the preset excitation order, the time-sequence adjustment amounts of the target slice groups are different from each other, and the time sequence adjustment amount of each of the target slice groups is less than a preset value. The preset value is determined based on the number of the slice groups.

Specifically, the time sequence of each target slice group is adjusted by a corresponding time-sequence adjustment amount based on the preset excitation order. Each time the time sequence of the target slice group is adjusted, the time sequences of some of the remaining slice groups may also change accordingly, therefore, it is based on the preset excitation order that the time sequences of the target slice groups are adjusted in sequence, to obtain the target excitation order. For the preset excitation order, the time-sequence adjustment amounts of the target slice groups are different. For example, the time-sequence adjustment amounts of the target slice groups may be reduced in sequence, so that the time sequences may be adjusted quickly and the impact is relatively small. The time-sequence adjustment amount of each target slice group is less than the preset value which is determined based on the number of the slice groups of the SMS excitations. For example, the preset value may be a time value of $T_{unit}\times(Ns/M_B/2-1)$, where Ns denotes the total number of the slices of the target object, $M_B$ denotes the number of the multiple simultaneously excited slices, $Ns/M_B$ denotes the number of the slice groups, $T_{uniit}=TR/(Ns/M_B)$ is the acquisition time period corresponding to the excitation of each of the slice groups and defined as the unit acquisition time, and TR denotes the repetition time. By adjusting the time sequence of the target slice groups in the above way, the target excitation order may be obtained quickly and accurately. By setting the time-sequence adjustment amount of each target slice group to be less than the preset value, it may be ensured that, in the target excitation order obtained through adjustment, the excitation time points of all slice groups, in each of which the smallest-numbered slice is an odd-numbered slice, are before the excitation time points of all slice groups in each of which the smallest-numbered slice is an even-numbered slice, or the excitation time points of all slice groups, in each of which the smallest-numbered slice is an odd-numbered slice, are after the excitation time points of all slice groups in each of which the smallest-numbered slice is an even-numbered slice. Moreover, the slices temporally adjacent in the adjusted excitation order, namely in the target excitation order, are prevented from being spatially adjacent, thereby reducing the inter-slice cross-talk.

In some embodiments, the preset excitation order is adjusted for the target slice group to obtain the target excitation order as follows: within each repetition time, starting from i=0, the slice groups including the slices with numbers $N_S/M_B\times1-i, \ldots, N_S/M_B\times(M_B-1)-i, N_S/M_B\times M_B-i$ are moved forward by $T_{unit}\times(Ns/M_B/2-2-i)$ in the time dimension; then the value of i is increased by adding 1, and if $Ns/M_B/2-2-i>0$, the adjustment process is repeated by moving the slice groups including the slices with numbers of $N_S/M_B\times1-i, \ldots, N_S/M_B\times(M_B-1)-i, N_S/M_B\times M_B-i$ forward by $T_{unit}\times(Ns/M_B/2-2-i)$ in the time dimension, till it is satisfied that $Ns/M_B/2-2-i=0$, and the adjustment ends. Taking $N_S=24$, and $M_B=2$ as an example, when i=0, it may be determined that the twelfth slice group including the slice 12 and the slice 24 in the preset excitation order is moved forward by four units of acquisition time to get the time sequence of these slices in the target excitation order. When i=1, it may be determined that the sixth slice group including the slice 11 and the slice 23 in the preset excitation order is moved forward by three units of acquisition time to get the time sequence of these slices in the target excitation order. When i=2, it may be determined that the eleventh slice group including the slice 10 and the slice 22 in the preset excitation order is moved forward by two units of acquisition time to get the time sequence of these slices in the target excitation order. When i=3, it may be determined that the fifth slice group including the slice 9 and the slice 21 in the preset excitation order is moved forward by one unit of acquisition time to get the time sequence of these slices in the target excitation order. After being sorted and optimized, the spatially adjacent slices are excited at a time interval of at least $5T_{unit}$ within each repetition time in the time dimension or between adjacent repetition times, so that the transition region between each excited slice and an adjacent slice thereof has sufficient longitudinal relaxation time, thereby reducing the inter-slice cross-talk to the greatest extent.

In one of the embodiments, after the step of obtaining the number of the slice groups of the SMS excitations of the target object, and before the step of acquiring the data of the SMS excitations of the target object to obtain the MR signals of each slice of the target object, the method further includes: performing the multi-band RF pulse on the target object based on the preset excitation order in response to a determination that the number of the slice groups is an odd number.

Specifically, when the number of the slice groups of the SMS excitations is odd, the acquiring manner of alternately exciting odd-and-even-numbered slices is used. In a relatively long repetition time (TR), firstly, the slice groups, in each of which the smallest-numbered slice is an odd-numbered slice, are excited in a slice-group sequence, and the corresponding MR signals are acquired at the same time. Then the slice groups, in each of which the smallest-numbered slice is an even-numbered slice, are excited in another slice-group sequence, and the corresponding MR signals are acquired at the same time. Alternatively, the slice groups, in each of which the smallest-numbered slice is an odd-numbered slice, are excited firstly, and then the slice groups, in each of which the smallest-numbered slice is an even-numbered slice, are excited, until all the slices are excited, and the corresponding MR signals are acquired while the slices are being excited. The numbers may be obtained by sequentially sorting slices based on the spatial positions of the slices to be imaged of the target object. In the acquiring manner of alternately exciting odd-and-even-numbered slices, within one repetition time, the excitation time points of the slice groups, in each of which the smallest-numbered slice is an odd-numbered slice, are all before excitation time points of the slice groups in each of which the smallest-numbered slice is an even-numbered slice, or the excitation time points of the slice groups, in each of which the smallest-numbered slice is an odd-numbered slice, are all after the excitation time points of the slice groups in each of which the smallest-numbered slice is an even-numbered slice. A slice has the same excitation order in all repetition times, for example, the slice 1 has the first excitation order in all repetition times TR. Slices that are excited simultaneously may be determined based on the total number of the slices and the number of the slice groups. The preset excitation order makes the excitation interval between slices adjacent in spatial positions be at least $T_{unit}\times floor(Ns/M_B/2)$ in the time dimension. By performing the multi-band RF pulse on the target object based on the preset excitation order in response to the determination that the number of slice groups is an odd number, each transition region between spatially adjacent slices has a longitudinal relaxation time of approximate TR/2, so that after the signal saturation of the transition region of the spatially adjacent slice is caused when a slice is excited, the saturated transition region has sufficient longitudinal relaxation time, thereby avoiding the inter-slice cross-talk and improving the quality of the acquired MR signals for the target object.

It should be understood that although all steps in the flowcharts involved in the above-mentioned embodiments are shown in an order as indicated by the arrows, these steps are not necessarily executed in the order indicated by the arrows. Unless explicitly stated in this text, there is no strict order restriction on the execution of these steps, and these steps may be executed in other orders. Moreover, at least some of the steps in the flowcharts involved in the above embodiments may include multiple steps or stages. These steps or stages are not necessarily executed at the same time, but may be executed at different time points. The execution order of these steps or stages is not necessarily sequential, but may be performed in turn or alternately with other steps or at least part of the steps or stages in other steps.

Based on the same inventive concept, an embodiment of the present application also provides a device for acquiring MR signal to implement the method for acquiring MR signal above. The solutions to the problem provided by this device are similar to the solutions recorded and implemented in the above method, therefore, the specific limitations of one or more embodiments of the device for acquiring MR signal provided hereinafter can be seen in the method for MR signal mentioned above, and they will not be repeated herein.

Figure 6:
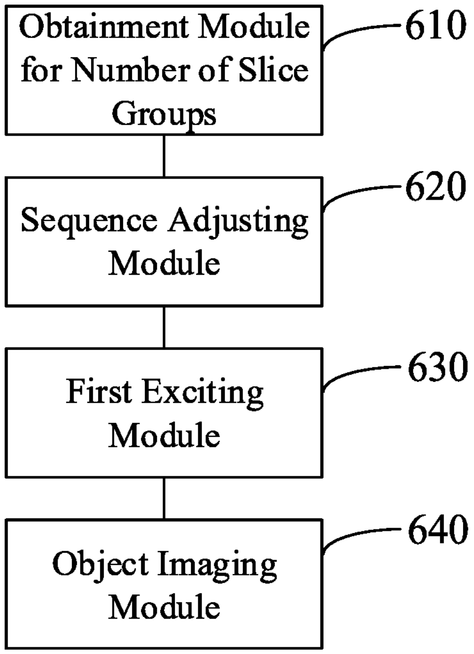
FIG. 6 is a block diagram showing a structure of a device for acquiring MR signal according to an embodiment of the present application.

In an embodiment, as shown in FIG. 6, a device for acquiring MR signal is provided. The device includes: an obtainment module for the number of slice groups 610, an excitation order adjusting module 620, a first excitation module 630, and an object imaging module 640.

The obtainment module for the number of slice groups 610 is configured to obtain the number of slice groups of SMS excitations of a target object. Each slice group includes multiple slices that are excited simultaneously by a radio frequency (RF) pulse.

The excitation order adjusting module 620 is configured to adjust a preset excitation order for a target slice group in response to a determination that the number of the slice groups is an even number, to obtain a target excitation order. In the target excitation order, slices spatially adjacent are not temporally adjacent. In one embodiment, the target slice group includes a firstly or finally excited slice group within each repetition time of the multi-band RF pulse.

The first excitation module 630 is configured to perform the multi-band RF pulse on the target object based on the target excitation order.

The object imaging module 640 is configured to acquire data of the SMS excitations of the target object to obtain MR signals of each slice of the target object. The MR signals of each slice are used for MRI of the target object.

In one of the embodiments, the obtainment module for the number of the slice groups 610 is also configured to obtain scanning parameters of the target object, where the scanning parameters include the number of slices simultaneously excited by the multi-band RF pulse at a time and the total number of slices of the target object. The obtainment module for the number of the slice groups 610 is further configured to determine the number of the slice groups based on the number of the simultaneously excited slices and the total number of the slices of the target object.

In one of the embodiments, the excitation order adjusting module 620 is further configured to determine a plurality of target slice groups based on the number of the slice groups and the number of slices simultaneously excited in each of the slice groups, and configured to adjust the time sequence of each of the target slice groups based on the preset excitation order to obtain the target excitation order.

In one of the embodiments, the excitation order adjusting module 620 is further configured to adjust the time sequence of each target slice group by a corresponding time-sequence adjustment amount based on the preset excitation order to obtain the target excitation order. For the preset excitation order, the time-sequence adjustment amounts of the target slice groups are different from each other, and the time sequence adjustment amount of each of the target slice groups is less than a preset value. The preset value is determined based on the number of the slice groups.

In one of the embodiments, the device for acquiring MR signal further includes a second excitation module.

The second excitation module is configured to perform the multi-band RF pulse on the target object based on the preset excitation order in response to a determination that the number of the slice groups is an odd number.

Each module in the above device for acquiring MR signal may be implemented in whole or in part by software, hardware, and a combination thereof. Each of the above modules may be embedded in or independent of the processor of the computer device in the form of hardware, or may be stored in the memory of the computer device in the form of software, so that the processor may call and execute the operations corresponding to the above modules.

In one of the embodiments, an MR scanning system is provided. The system includes an MR scanning device and a processing unit connected to the MR scanning device. The MR scanning device is configured to emit a multi-band RF pulse to perform SMS excitations on the target object, and to acquire data of the SMS excitations of the target object and obtain MR signals of each slice of the target object. The processing unit stores a computer program, and the processing unit, when executing the computer program, performs the steps of the above method.

In one of the embodiments, a processing unit is provided. The processing unit may be a terminal, and its internal structure diagram may be shown in FIG. 7. The processing unit includes a processor, a memory, an input/output interface, a communication interface, a display unit, and an input device. The processor, the memory, the input/output interface are connected through a system bus. The communication interface, the display unit, and the input device are connected to the system bus through the input/output interface. The processor of the processing unit is configured to provide computing and control capabilities. The memory of the processing unit includes a non-transitory storage medium and an internal memory. The non-transitory storage medium stores an operating system and executable instructions. The internal memory provides an environment for the operation of the operating systems and the computer programs in the non-transitory storage medium. The input/output interface of the processing unit is configured to exchange information between the processor and external devices. The communication interface of the processing unit is configured to communicate with the external terminals in a wired or wireless mode, and the wireless communication can be realized by WIFI, mobile cellular network, near field communication (NFC), or other technologies. The computer programs, when being executed by the processor, implement the method for acquiring MR signal. The display unit of the processing unit is configured to form a visually visible picture, and may be a display screen, a projection device, or a virtual reality imaging device. The display screen may be an LED or e-ink display, and the input device of the processing unit may be a touch layer covering the display screen, or a key, trackball or trackpad arranged on the housing of the processing unit, or an external keyboard, trackpad or mouse, etc.

Figure 7:
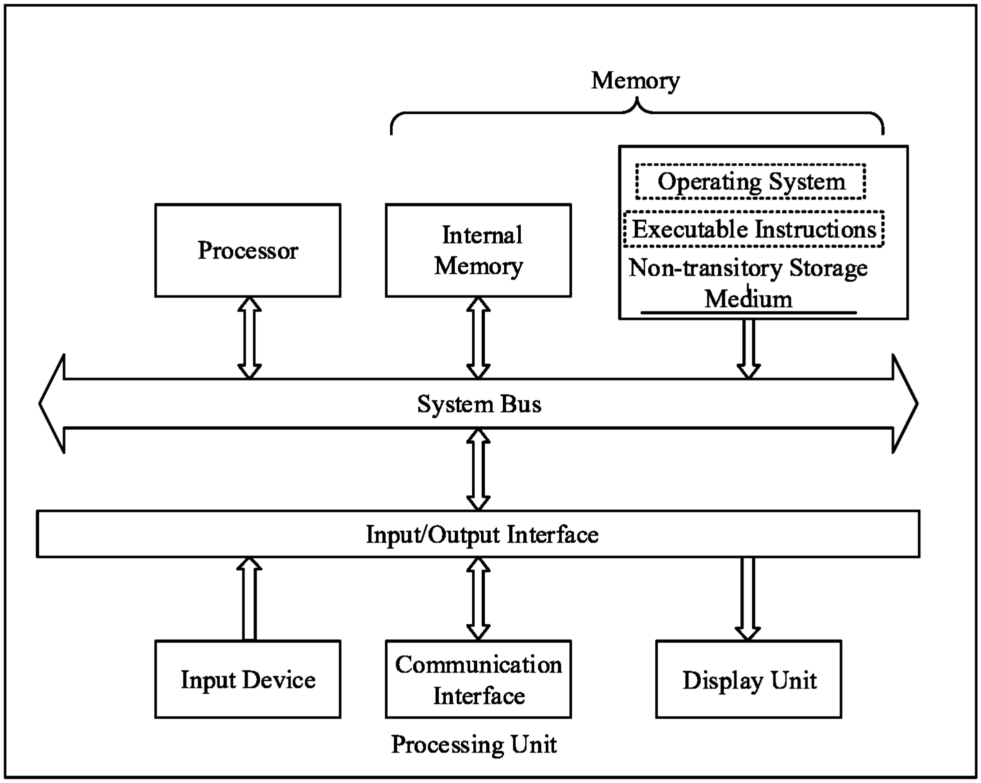
FIG. 7 is a block diagram showing an internal structure of a processing unit according to an embodiment of the present application.

Those skilled in the art may understand that the structure shown in FIG. 7 is only a block diagram showing a partial structure related to the solutions of the present application, and does not constitute a limitation on the computer equipment to which the solutions of the present application is applied. A specific computer equipment may include more or fewer parts than those shown in the figure, or combine certain parts, or have a different arrangement of parts shown in the figure.

In one of the embodiments, a non-transitory computer-readable storage medium is provided. The non-transitory computer-readable storage medium has executable instructions stored thereon, and the executable instructions, when being executed by the processor, causes the processor to perform the steps of the above method.

In one embodiment, a computer program product is provided. The computer program product includes a computer program, and the computer program, when being executed by a processor, causes the processor to perform the steps of the method above.

Those ordinary skilled in the art may understand that all or part of the process in the method of the above embodiments may be implemented by instructing the relevant hardware through executable instructions, and the executable instructions may be stored in a non-transitory computer-readable storage medium. The executable instructions, when being executed, may include the processes of the embodiments of the methods above. Where, any reference to memory, storage, database, or other media used in the various embodiments provided in this application may include at least one of non-transitory and transitory memory. Non-transitory memory may include read-only memory (ROM), magnetic tape, floppy disk, flash memory, or optical memory, high-density embedded non-transitory memory, resistance random access memory (ReRAM), magneto resistive random-access memory (MRAM), ferroelectric random-access memory (FRAM), phase change memory (PCM), graphene memory, and the like. The transitory memory may include random access memory (RAM) or external cache memory. By way of illustration and not limitation, the RAM may be in various forms, such as static random-access memory (SRAM) or dynamic random-access memory (DRAM), etc. The databases involved in the embodiments provided in the present application may include at least one of a relational database and a non-relational database. The non-relational databases may include, but are not limited to, a blockchain-based distributed database, and the like. The processors involved in the embodiments provided in the present application may be, but are not limited to, a general-purpose processor, a central processing unit, a graphics processor, a digital signal processor, a programmable logic, a quantum-computing-based data processing logic, and the like.

The technical features of the embodiments above may be combined arbitrarily. To make the description concise, not all possible combinations of the technical features in the above embodiments are described. However, as long as there are no contradictions in the combinations of these technical features, all of the combinations should be considered to be within the scope of the specification.

The embodiments above only represent several implementation modes of the present application, and the description thereof is relatively specific and detailed, but it should not be construed as limiting the scope of the patent. It should be noted that for those skilled in the art, various modifications and improvements may be made without departing from the concept of the present application, and all these modifications and improvements belong to the protection scope of the present application. Therefore, the scope of protection of the patent application should be subject to the appended claims.

What is claimed is:

1. A method for acquiring magnetic resonance (MR) signal, comprising:

obtaining a number of slice groups of simultaneous multi-slice (SMS) excitations of a target object, each of the slice groups comprising multiple slices excited simultaneously by a multi-band radio frequency (RF) pulse;

setting a preset excitation order;

adjusting the preset excitation order for a plurality of target slice groups in response to a determination that the number of the slice groups is an even number to obtain a target excitation order, comprising:

determining the plurality of target slice groups based on the number of the slice groups and the number of the multiple slices simultaneously excited in each of the slice groups comprising: determining slice groups comprising slices numbered with $N_S/M_B \times n-i$ to be the plurality of target slice groups, wherein: Ns denotes a total number of the slices of the target object; MB denotes the number of the multiple simultaneously excited slices; $Ns/M_B$ denotes the number of the slice groups; i is any integer from 0 to $N_S M_B/2-3$; and n is any integer from 1 to MB; and adjusting a time sequence of each of the plurality of target slice groups by a time-sequence adjustment amount of each of the plurality of target slice groups based on the preset excitation order to obtain the target excitation order comprising: moving the time sequences of the plurality of target slice groups comprising the slices numbered with $N_S/M_B \times n-i$ forwards by time values of $T_{unit} \times (Ns/M_B/2-2-i)$ respectively to obtain the target excitation order, wherein $T_{unit}=TR/(Ns/M_B)$ is an acquisition time period corresponding to an excitation of each of the slice groups and defined as a unit acquisition time; and TR denotes a repetition time; wherein the time-sequence adjustment amounts of the plurality of target slice groups for adjusting the preset excitation order are different from each other, the time sequence adjustment amount of each of the plurality of target slice groups is less than a preset value, the preset value is determined based on the number of the slice groups, and spatially adjacent slices are not temporally adjacent after the preset excitation order is adjusted;

performing the multi-band RF pulse on the target object based on the target excitation order; and acquiring data of the SMS excitations of the target object to obtain the MR signals of each slice of the target object, the MR signals of each slice being used for magnetic resonance imaging (MRI) of the target object.

2. The method according to claim 1, wherein the obtaining the number of the slice groups of the SMS excitations of the target object comprises:

obtaining scanning parameters of the target object, the scanning parameters comprising the number of slices simultaneously excited by the multi-band RF pulse and a total number of slices of the target object; and determining the number of the slice groups based on the number of the simultaneously excited slices and the total number of the slices of the target object.

3. The method according to claim 1, wherein:

the setting the preset excitation order comprises:

sequentially numbering slices of the target object with continuous natural numbers respectively based on a spatial position of each of the slices of the target object; and arranging excitation time points of slice groups, in each of which a smallest-numbered slice is an odd-numbered slice, to be before excitation time points of other slice groups within each repetition time, or arranging the excitation time points of the slice groups, in each of which the smallest-numbered slice is the odd-numbered slice, to be after the excitation time points of the other slice groups within each repetition time; and a slice-number difference of each two slices simultaneously excited in a same slice group is an integer multiple of the number of the slice groups.

4. The method according to claim 3, wherein the plurality of target slice groups comprise a slice group firstly or finally excited within each repetition time.

5. The method according to claim 1, wherein the preset value is determined based on a total number of the slices of the target object, the number of the multiple simultaneously excited slices, the number of the slice groups, an acquisition time period corresponding to an excitation of each of the slice groups, and a repetition time.

6. The method according to claim 1, wherein after the obtaining the number of slice groups of the simultaneous multi-slice (SMS) excitations of the target object, and before the acquiring the data of the SMS excitations of the target object to obtain the magnetic resonance (MR) signals of each slice of the target object, the method further comprises:

performing the multi-band RF pulse on the target object based on the preset excitation order in response to a determination that the number of the slice groups is an odd number.

7. A magnetic resonance (MR) scanning system, comprising:

an MR scanning device configured to emit a multi-band radio frequency (RF) pulse to perform simultaneous multi-slice (SMS) excitations on a target object, and configured to acquire data of the SMS excitations of the target object to obtain MR signals of each slice of the target object;

a processing unit connected to the MR scanning device and having a computer program stored therein, wherein, the processing unit, when executing the computer program, performs:

obtaining a number of slice groups of simultaneous multi-slice (SMS) excitations of a target object, each of the slice groups comprising multiple slices excited simultaneously by a multi-band radio frequency (RF) pulse;

setting a preset excitation order;

adjusting the preset excitation order for a plurality of target slice groups in response to a determination that the number of the slice groups is an even number to obtain a target excitation order, comprising:

determining the plurality of target slice groups based on the number of the slice groups and the number of the multiple slices simultaneously excited in each of the slice groups comprising: determining slice groups comprising slices numbered with $N_S/M_B \times n-i$ to be the plurality of target slice groups, wherein: Ns denotes a total number of the slices of the target object; $M_B$ denotes the number of the multiple simultaneously excited slices; $Ns/M_B$ denotes the number of the slice groups; i is any integer from 0 to $N_S/M_B/2-3$; and n is any integer from 1 to $M_B$; and adjusting a time sequence of each of the plurality of target slice groups by a time-sequence adjustment amount of each of the plurality of target slice groups based on the preset excitation order to obtain the target excitation order comprising: moving the time sequences of the plurality of target slice groups comprising the slices numbered with $N_S/M_B \times n-i$ forwards by time values of $T_{unit} \times (Ns/M_B/2-2-i)$ respectively to obtain the target excitation order, wherein $T_{unit}=TR/(Ns/M_B)$ is an acquisition time period corresponding to an excitation of each of the slice groups and defined as a unit acquisition time; and TR denotes a repetition time; wherein the time-sequence adjustment amounts of the plurality of target slice groups for adjusting the preset excitation order are different from each other, the time sequence adjustment amount of each of the plurality of target slice groups is less than a preset value, the preset value is determined based on the number of the slice groups, and spatially adjacent slices are not temporally adjacent after the preset excitation order is adjusted;

performing the multi-band RF pulse on the target object based on the target excitation order; and acquiring data of the SMS excitations of the target object to obtain the MR signals of each slice of the target object, the MR signals of each slice being used for magnetic resonance imaging (MRI) of the target object.

8. The MR scanning system according to claim 7, wherein the obtaining the number of the slice groups of the SMS excitations of the target object comprises:

obtaining scanning parameters of the target object, the scanning parameters comprising the number of slices simultaneously excited by the multi-band RF pulse and a total number of slices of the target object; and determining the number of the slice groups based on the number of the simultaneously excited slices and the total number of the slices of the target object.

9. The MR scanning system according to claim 7, wherein:

the setting the preset excitation order comprises:

sequentially numbering slices of the target object with continuous natural numbers respectively based on a spatial position of each of the slices of the target object; and arranging excitation time points of the slice groups, in each of which a smallest-numbered slice is an odd-numbered slice, to be before excitation time points of other slice groups within each repetition time, or arranging the excitation time points of the slice groups, in each of which the smallest-numbered slice is an odd-numbered slice, to be after the excitation time points of the other slice groups within each repetition time; and a slice-number difference of each two slices simultaneously excited in a same slice group is an integer multiple of the number of the slice groups.

10. The MR scanning system according to claim 9, wherein the plurality of target slice groups comprise a slice group firstly or finally excited within each repetition time.

11. A non-transitory computer-readable storage medium, having executable instructions stored thereon, wherein the executable instructions, when being executed by a processor, causes the processor to perform steps of the method of claim 1.

12. A computer program product, comprising a computer program, wherein the computer program, when being executed by a processor, causes the processor to perform steps of the method of claim 1.

* * * * *